United States Patent [19]

Fruitstone et al.

[11] 4,247,536
[45] Jan. 27, 1981

[54] METHOD OF PREPARING C3-SENSITIZED ERYTHROCYTES

[75] Inventors: Mitchell J. Fruitstone; José Carro; Betty G. Pixton, all of Miami, Fla.

[73] Assignee: American Hospital Supply Corporation, Evanston, Ill.

[21] Appl. No.: 890,558

[22] Filed: Mar. 20, 1978

[51] Int. Cl.³ .................... G01N 33/48; G01N 33/68
[52] U.S. Cl. .................................. 424/12; 23/230 B; 424/11; 424/13
[58] Field of Search .................. 424/8, 11, 12, 13; 23/230 B

[56] References Cited

U.S. PATENT DOCUMENTS 4,092,114   5/1978   Buck ............................. 23/230 B

OTHER PUBLICATIONS

Frommel, Immunol., vol. 13, 1967, pp. 501–508.
LoBuglio, Science, vol. 158, Dec. 22, 1967, pp. 1582–1585.
Huber, Science, vol. 162, Dec. 13, 1968, pp. 1281–1283.
Huber, Fed. Proc., vol. 29, 1970, Ab. No. 2109.
Nusbacher, The J. of Immunol., vol. 108, 1972, pp. 803–902.
Garratty, Transfusion, vol. 16, 1976, pp. 297–306.
Moore, Transfusion, vol. 14, 1974, pp. 416–424.
Kwapinski, Method of Immunochem & Immunol. Res. Intersci., Pub. N.Y., 1972, pp. 245–247, 416–419, 422–429, 430–439.
Rosse et al., The J. of Clin. Invst., vol 53, 1974, pp. 31–43.
Freedman et al., Vox. Sang., vol. 31, 1976, pp. 241–257.
Bolotin et al., Biochemistry, vol. 16, 1977, pp. 2008–2015.
Logue et al., The J. of Clin. Invst., vol. 52, 1973, pp. 493–501.
Schreiber et al., The J. of Clin. Invst., vol 51, 1972, pp. 575–589.
Gilliland et al., The J. of Clin. Invst., vol. 49, 1970, pp. 898–906. C4-sensitized Primary Examiner—Anna P. Fagelson
Attorney, Agent, or Firm—Edward A. Figg; Robert E. Hartenberger

[57] ABSTRACT

A set of four cell suspensions containing erythrocytes monospecifically sensitized with IgG, IgM, C3, and C4. The suspensions provide control cells to determine the purity and strength of the antibodies to these immunoglobins or complement components contained in antisera used for clinical testing. Strict control of the pH, temperature, and EDTA concentration of a solution to which blood is added allows for the elective production of C3- or C4-sensitized cells. Selecting a serum with IgG or IgM antibodies and inactivating undesired proteins permits the production IgG- or IgM-sensitized cells. The resultant cells have agglutination reaction strengths of about 2–4+. Erythrocytes from humans or other animals may undergo the monospecific sensitization. Other human proteins, such as IgA or C5, and plasma proteins from other animals may similarly be attached monospecifically to red blood cells.

11 Claims, No Drawings

METHOD OF PREPARING C3-SENSITIZED ERYTHROCYTES

BACKGROUND

Clinical tests using antigen-antibody reactions have become increasingly important in the diagnoses of various human ailments. This type of testing, of course, also proves invaluable in blood compatibility determinations performed prior to transfusions. It not only, in general, assures the blood's suitability for the recipient (patient), but also screens for unexpected antibodies in the donor and the recipient.

Other conditions also benefit from the use of clinical tests based upon antigen-antibody reactions. These tests find important use for immunologic disease states such as immune hemolytic anemias due to drug-antidrug complexes. Other examples include autoimmune hemolytic anemia, erythroblastosis fetalis, and transfusion reactions resulting from incompatible blood.

In direct testing procedures, an antiserum containing antibodies to human immunoglobulin(s) and/or complement component(s) receives the erythrocytes undergoing testing. Agglutinated cells in the test indicate the presence immunoglobulin(s) and/or complement component(s) on the erythrocytes. The testing procedure usually includes one or more controls to insure the proper reactivity of the reagents.

In indirect testing, the patient's serum typically undergoes incubation with red blood cells. The incubation allows antibodies in the serum to attach to antigenic sites on the erythrocytes. The cells, after removal of the patient's serum by washing upon completion of incubation, undergo testing with a serum containing antibodies to immunoglobulin(s) and/or complement component(s). This step resembles the direct testing procedures discussed above. The agglutination of the erythrocytes in the last step indicates the presence of the corresponding immunoglobulin(s) and/or complement component(s) on the erythrocytes, and indicates the presence of antibodies to antigens on the erythrocyte surface. Again, the use of controls minimizes false results.

The antiserum used in the tests may take one of two forms. The classical, or polyspecific, antiserum generally contains antibodies to a wide range of immunoglobulins and complement components. In either the direct or indirect procedure, if the erythrocytes have become sensitized (coated) with any of these immunoglobulins or complement components, agglutination will occur and give a positive test result. The specific immunoglobulin(s) and/or complement component(s) that produced the positive result, however, remain unknown with the use of this polyspecific type of antiserum.

Most, if not all, of the tests employing polyspecific antiserum will provide additional pertinent information if repeated with monospecific antisera. In comparison to the polyspecific antiserum, these latter reagents contain an antibody for a single immunoglobulin class or complement component. Agglutination occurs, of course, only if the erythocytes' surfaces contain the specific immunoglobulin or complement component corresponding to the antibody in the antiserum.

The reliability of the direct and indirect testing procedures depends heavily upon the concentrations of the antibodies in both the polyspecific and monospecific antisera. Moreover, the purity (degree of monospecificity) of the single antibody in each of the monospecific antisera represents an important criterion in assuring the accuracy of the results of analyses employing them.

However, the antibodies in the antisera represent esoteric proteins which may readily undergo denaturation and degeneration. This can occur as a result merely of the passage of time or of even slightly improper storage conditions. These deleterious occurrences can unfavorably alter the nature of either the polyspecific or monospecific antisera.

Thus, the strengths of the antibodies in the antisera must remain known in order for the results of tests employing the antisera to have validity. This required knowledge involves two separate aspects for any particular antiserum. The specific immunoglobulin(s) and/or complement component(s) with which its antibodies will react represents a first crucial aspect of the antiserum. Furthermore, the reactive strength of the antiserum towards its corresponding protein must be known in order to provide meaningful test results. And, the reactive strengths of a polyspecific antiserum to each of its corresponding immunoglobulins and complement components must remain controlled to avoid inaccurate results.

Determining the antibodies and their reactive strengths in the antiserum does not represent a classical chemical problem. An antibody molecule generally can react with only a specific single amino-acid group on an immunoglobulin molecule or complement molecule. Thus, different antibodies react with different amino-acid combinations and, therefore, different immunoglobulins or complement components. However, antibodies with different specificities have basic chemical structures which are very similar. Present chemical knowledge lacks the tools to differentiate between the different antibodies for the different immunoglobulins and complement components on the basis of molecular structure. Yet, the antibodies that correspond to the different proteins do, in fact, possess differencs. They display reactivity only with their single corresponding immunoglobulin or complement component.

Thus, the only readily definable difference between the different antibodies centers upon the reactivity of each with their separate protein; the only indication of the presence of an antibody for a particular immunoglobulin, for example, requires the reaction of that antibody with that immunoglobulin. One commonly used method for detecting this reaction involves the agglutination of erythrocytes to which the particular protein or immunoglobulin has attached itself. For example, by this method determining the presence of the antibody for the IgG immunoglobulin in an antiserum requires reacting that antiserum with erythrocytes having IgG molecules attached to them. Any resulting agglutination and the strength of that agglutination will show the presence and reactive strength of the antibody in the antiserum.

Thus, the need for erythrocytes having a single attached immunoglobulin class or complement component becomes clear. Such cell preparations would assume an absolutely crucial role in determining the presence and reactive strengths of antibodies in both polyspecific and monospecific antisera. These cell preparations would thus assure the suitability of these antisera for their important clinical tests.

While the need for red cell preparations having a single immunoglobulin class or complement component has become clear, their preparation has eluded success. Various attempts at making red blood cell suspensions having a single attached protein have not achieved their objective. For example, the "low ionic-strength method" of J. A. Moore and H. Chaplin, Jr., in their article "Anti-C3d Antiglobulin Reagents. II. Preparation of an Antiglobulin Serum Monospecific for C3d" appearing in *Transfusion*, 14:416 (1974), attempts to produce erythrocytes having only the C3 complement component attached. However, as shown in the article of G. Garratty and L. Petz, "The Significance of Red Cell Bound Complement Components in Development of Standards and Quality Assurance for the Anti-Complement Components of Antiglobulin Sera" appearing in *Transfusion*, 16:297 (1976), these procedures result in cells sensitized with detectable immunoglobulins as well as other complement components. Moreover, the reactive strength of the desired complement component is not always at the desired level. Thus, the need for cell suspensions having a single attached protein has remained unfilled.

SUMMARY

To provide a useful standard against which to measure antisera, the cells in a suspension should be sensitized with molecules of one human immunoglobulin class or one complement component. Moreover, the cells in the suspension should remain devoid of any other immunoglobulin or complement component detectable by erythrocyte agglutination. The proteins constituting the important class of immunoglobulins and complement components include the IgG, IgM and IgA immunoglobulins and the C3, C3b, C3d, C4, C4b, C4d and C5 complement components and subcomponents.

Naturally, the cells should be suspended in an aqueous solution isotonic to the erythrocytes. This will prevent lysis of the red blood cells.

Typically, the erythrocytes in the suspension should have received sensitization with exactly one protein from the group listed above. In particular, they normally will not display any substantial sensitization to any other protein in that group. Such monosensitized cells will provide a very specific test for the presence and reactive strength of a single antibody specificity in an antiserum. That antibody, of course, will correspond to the single immunoglobulin, complement component or subcomponent with which the cells have undergone sentitization.

Frequently, these proteins have the ability to break down into subcomponents within or outside of the organism concerned. These cleavages probably represent normal reactions. An antiserum containing antibodies for the protein itself may also, consequently, display reactivity towards that protein's subcomponents. Accordingly, a suitable cell suspension, to act as a control for this antiserum, may include, attached to the erythrocytes, one or more subcomponents of the protein or the intact protein. Under these conditions, no other protein should sensitize the same cells.

Naturally, a clinical laboratory would require a suspension having a human serum protein attached to the erythrocytes. Such a suspension should include red blood cells sensitized with one of the human proteins in the class given above. The more important members of this class include the IgG, IgM, C3, and C4 proteins. Facilities for other animals would, on the other hand, make use of suspensions containing proteins appropriate to the species it deals with.

Polyspecific, oligospecific and monospecific antisera must contain known reactivities to immunoglobulins and/or complement cmponents corresponding to the erythrocyte sensitization. The polyspecific serum will demonstrate reactivity towards immunoglobulin(s) and complement component(s). An oligospecific serum possesses reactivity towards either immunoglobulins or complement components, but not both. A monospecific serum, while possessing reactivity towards only one immunoblobulin or complement component, will display a lack of reactivity towards the others.

Thus, obtaining an accurate determination of specifity(ies) of these types of antisera requires tests for their reactivities with several different proteins bound to erythrocytes. Each of these proteins, of course, must be attached to erythrocytes provided in a separate suspension from the erythrocytes sensitized with the other proteins. Thus, the lab typically will have need for a set of cell suspensions with each containing erythrocytes sensitized with a single immunoglobulin class or complement component.

The set of several cell suspensions, with each suspension incorporating a different protein, would primarily find use in clinical laboratory facilities. Accordingly, each suspension would include erythrocytes suspended in a aqueous isotonic solution and sensitized with a single human protein. In almost all instances, the erythrocytes would have undergone sensitization with a globulin detectable by agglutination in the usual antiglobulin testing. For convenience, the sensitization of the erythrocytes should suffice to provide an agglutination reaction strength of about 2-4+.

The more important human serum proteins include the IgG and the IgM immunoglobulins, and the C3 and the C4 complement components. With regards to the immunoglobulins, only IgG and IgM appear capable of directly activating the classical complement pathway upon binding to an antigen. Moreover, most erythrocytes' antigen-antibody reactions involve immunoglobulins of these classes.

With regards to the complement components, the classical pathway of complement activation involves early participation of C4. Consequently, antisera have often included anti-C4 either as one of many in a polyspecific serum or as the only protein in a monospecific serum forming part of a set. However, the antibodies corresponding to C3 have greater importance. The complement pathway results in the activation of up to 1000 C3 molecules for each C4 molecule involved in the process. Thus, a serum containing antibody to C3 would appear to have a significantly greater likelihood of detecting bound complement than the serum with anti-C4.

Accordingly, polyspecific and monospecific sera, containing antibodies for the IgG and IgM immunoglobulins and the C3 and C4 complement components can serve an important function in clinical laboratories. The testing of such sera to demonstrate the continued predictable reactivity of the antobodies thus involves the use of four cell suspensions. Each suspension should include erythrocytes sensitized with one of these four important proteins.

The preparation of these suspensions involves the attachment of the immunoglobulins or complement components to the surface of the cells. That in turn requires the presence on the cells of complement receptors and antigens to which the immunoglobulins, as antibodies, can attach. Accordingly, the erythrocytes may derive from any animal to which the normal human can make antibodies. Typically, a mammal will provide such erythrocytes. Particularly good examples, of course, include rabbits, goats, horses, and human beings, with the first and fourth members of that group finding most frequent use.

Attaching the different complement proteins to the erythrocytes generally follow procedures that closely resemble each other. Strictly controlling the conditions under which the reactions proceed, however, allows for the sensitization of the erythrocytes with one complement component to the exclusion of others.

Thus, for example, sensitizing erythrocytes with C3 or C4 should begin in a solution having approximately 8.0 to 10.0 w./v. percent sucrose and a predetermined concentration of EDTA generally falling within the range of about 0.10 to 50.0 millimolar. Normally, the EDTA would take the form of $Na_2EDTA.2H_2O$ in an approximately 2.5 to 20 millimolar concentration. The temperature of the solution should fall between about 0° to 37° C. The solution should also have a pH of about 4.5 to 8.0. A buffer in an approximately 0.1 to 25 millimolar concentration will maintain the solution in this desired pH range. For the sensitization with C3 and C4 complement components, the pH should generally not go outside of the range of 5.1 to 7.0. Utilizing $Na_2HPO_4$—$NaH_2PO_4.H_2O$ as the buffer in a 4.9 to 5.1 millimolar concentration should serve to maintain the pH at the value needed for the reaction.

This carefully prepared solution then receives a small amount of a suspension of erythrocytes in a physiologic liquid. The erythrocytes incubate in this solution maintained at the specific preselected temperature. After the incubation, the erythrocytes are removed from the solution, washed, and resuspended in a red cell preservative medium.

To sensitize erythrocytes with the C3 protein, the solution generally has a pH very close to 5.1, an 8.4 millimolar concentration of $Na_2EDTA.2H_2O$, and a temperature of about 0° C. Approximately one volume of whole blood having an added anticoagulant combines with 19 volumes of the solution to initiate the sensitization reaction.

In comparison, the attachment of the C4 protein usually proceeds in a solution having a pH of about 7.0. The $Na_2EDTA.2H_2O$ has an approximately 2.8 millimolar concentration, and the solution has a temperature of about 37° C.

Rather than merely adding whole blood as with the C3 sensitization procedure, the solution receives a modified erythrocyte suspension. To prepare it, a physiologic saline liquid replaces approximately 4/5 of the blood's original plasma volume. Again, however, one volume of the modified erythrocyte suspension combines with 19 volumes of the C4-procedure solution to allow for the attachment of that protein.

The preparation of the IgG and the IgM cell suspensions also proceed along somewhat similar pathways. The former begins by inactivating any IgM agglutinins present in an antiserum possessing an antibody of the IgG class. To facilitate this step, the antiserum should originally have very little, if any, IgM agglutinins present with specificities for the surface antigens of the erythrocytes selected for sensitization.

A solution, devoid of interfering IgM proteins and at a temperature of about 37° C., may then receive whole blood or washed erythrocytes suspended in a physiologic solution. To permit the sensitization to occur, the erythrocytes must possess the antigen corresponding to the selected IgG antibody. Conveniently, the physiologic solution containing the erythrocytes may simply take the form of blood having an added anticoagulant. The actual sensitization with the IgG protein involves incubating the erythrocytes in the antiserum at a temperature of approximately 37° C. for a period of at least 15 minutes. Afterwards, the completion of the preparation involves separating the erythrocytes from the antiserum and washing them.

Two procedures have generally proved acceptable for inactivating any IgM protein present in the antiserum. First, the antiserum may undergo heating for a period of about 30 to 60 minutes at a temperature of about 56° to 60° C. Alternatively, the antiserum may be treated with a mild reducing agent. Suitable agents for this purpose include 2mercaptoethanol, dithiothreitol, and dithioerythritol.

The IgM sensitization procedure requires an antiserum containing an antibody of the IgM class and substantially no IgG red cell agglutinins with specificities for the surface antigens of the erythrocytes selected for sensitization. Any C3 or C4 proteins contained in the antiserum, however, should first undergo inactivation.

Conveniently, adding to the antiserum a primary amine or a compound producing ammonia in the antiserum inactivates C3 and C4 proteins. Examples of suitable compounds include ammonium hydroxide, ammoniun chloride, and hydrazine. The selected compound should remain in the serum at a pH of about 8 for a period of at least 30 minutes.

After the inactivation of C3 and C4 proteins, the antiserum, while at a temperature of about 37° C., may then receive washed erythrocytes. The cells incubate in the antiserum at a temperature of 37° C. for a period of about 15 to 60 minutes while receiving gentle stirring. The removal of the erythrocytes from the antiserum and a thorough washing follows the incubation to complete the sensitization procedure.

In either the IgG or the IgM procedures, the washing of the erythrocytes involves their repeated suspension in and removal from a red cell preservative medium. Moreover, the appropriate antiserum, prior to receiving the erythrocytes, should have a concentration that can produce cells having a desired level of reactivity. Typically, the cells, when mixed with undilute serum having an antibody of the IgG or IgM class, as appropriate, should result in a 2-4+ reaction. No less than a 1+ reactivity should occur with a 1:4 dilution of the same serum. Where the initial reactant antiserum would produce overly reactive erythrocytes, it should undergo sufficient dilution prior to sensitization to produce the desired reactivity.

DETAILED DESCRIPTION

1. Preparation of IgG-Sensitized Erythrocytes

The serum employed in the procedure should contain an antibody of the IgG class and little or no detectable IgM red-cell agglutinins with specificities for the surface antigens of the erythrocytes selected for sensitization. For example, the serum may contain anti-$Rh_o(D)$, which agglutinates $Rh_o(D)$ positive red cells in a high protein medium at 37° C. or at the antiglobulin phase. The agglutination should not normally proceed in saline solutions at room temperature. The techniques for selecting the appropriate serum and for many of the other steps in this and the following procedures appear in the recent editions of the standard reference work, *Technical Methods and Procedures of the American Association of Blood Banks.*

Any IgM agglutinins that may appear in the antiserum should be inactivated prior to the sensitization of the erythrocytes. Two methods generally suffice to accomplish this task. First, the antiserum may undergo heating in a water bath to approximately 50° to 60° C. for a period of approximately 30 to 60 minutes. During that time, it should receive frequent or continuous stirring. Alternatively, adding reducing agents to the antiserum will destroy the undesired IgM proteins. Suitable examples of such agents include 2-mercaptoethanol, dithiothreitol, or dithioerythritol.

In order to receive the erythrocytes, the antiserum should enter a container having a stirrer. The container should sit in a 37° C. water bath for a sufficient period to bring contents to that temperature.

The erythrocytes used in the procedure should derive from whole blood collected from a healthy donor, typically group O. They should test positively for the antigen corresponding to the antibody selected. Thus, for example, the erythrocytes should be $Rh_o(D)$ positive when employing anti-D. The blood should, of course, receive a suitable anticoagulant such as CPD or be defibrinated. The sensitization procedures should occur on the day of collection. Until that time, the blood should remain at a temperature of about 35° to 37° C. prior to its use to avoid the binding of cold autoantibodies such as auto anti-I and fixation of complement.

While undergoing gentle stirring, the warm antiserum receives an approximately equal volume of the thoroughly mixed anticoagulated or defibrinated whole blood. The combined antiserum and blood then incubates for about 60 minutes at 37° C. with constant, gentle stirring.

Centrifugation at 2° to 8° C. will then pack the cells and permit the removal of the supernatant. The erythrocytes, now sensitized, should undergo resuspension in at least four volumes of cold (2° to 8° C.) red cell preservative medium. Thorough mixing should then precede centrifugation and decanting or aspiration as above. This washing procedure should occur at least three additional times so that the cells will have experienced it a total of at least four times.

The washed, sensitized erythrocytes are resuspended in sufficient red cell preservative medium to provide them in a final concentration of about 2 to 5 percent. This final suspension of the monospecifically sensitized cells should be stored at a temperature of about 2° to 8° C. when not in use.

The sensitized cell suspension then undergoes testing with monospecific antihuman sera. These test sera would normally include anti-IgG (q-chain specific), anti-IgM ($\mu$-chain specific), anti-C3, and anti-C4. To conduct the test, properly labeled test tubes should each receive one drop of one of the antisera. One drop of the cell suspension also enters each test tube. The test solutions then undergo centrifugation at 1000 rcf for approximately 15 to 20 seconds. Negative reactions should occur with the anti-IgM ($\mu$-chain specific), anti-C3, and anti-C4 antisera. The test with the anti-IgG ($\gamma$-chain specific) should yield a 2–4+ reaction with undiluted antiserum. A 1:4 dilution of the anti-IgG antiserum should yield at least a 1+ reaction.

The foregoing procedure presumed a sufficient familiarity with the particular reactant antiserum used in the sensitization procedure to produce cells having the reactivities given above. Where such knowledge about the antiserum is lacking, it should undergo testing to determine its appropriate concentration to provide these reactivities. The test procedure involves serially diluting the antiserum in a suitable red cell preservative medium containing EDTA such as DADE Reverse Cyte ® Diluent manufactured by DADE Division, American Hospital Supply Corporation of Miami, Florida. Each of the dilutions undergoes the complete sensitization with erythrocytes given above. The dilution providing the appropriately reactive erythrocytes is then used to produce the final sensitized cell suspension.

2. Preparation of IgM-Sensitized Erythrocytes

The serum used in this procedure should contain an antibody of the IgM glass and little or no detectable IgG red cell agglutinins with specificities for the surface antigens of the erythrocytes selected for sensitization. An anti-$Le^a$ serum that agglutinates $Le^a$ positive red cells in saline at room temperature could represent such an anitserum. However, the antiserum should not agglutinate these erythrocytes in a high protein medium at 37° C. or at the antiglobulin phase when tested with anti-IgG ($\gamma$-chain specific).

Any C4 in the serum could become affixed to the erythrocytes by the classical complement pathway. Accordingly, the preparation of the antiserum for the sensitization procedure includes inactivating any C4 present. Adding a source of ammonia, hydrazine, or similar compounds will accomplish the task. Ammonium chloride represents a suitable example. When using it, a 0.03 N. $NH_4Cl$ solution should have its pH adjusted to about 8 with 1 N. NaOH. Four volumes of serum should then receive one volume of this $NH_4Cl$ solution and be combined at room temperature for approximately 30 to 90 minutes. The treated serum should then receive approximately 0.1 to 1.0 volume of EDTA in a one to twenty millimolar concentration. A six millimolar concentration of dipotassium EDTA at pH 7 performs as required.

To proceed further with the erythrocyte sensitization, a container with a stirrer should receive the antiserum. It then sits in a 37° C. water bath until the contents reach that temperature.

A healthy donor, typically group O, should provide the whole blood used for the procedure. His erythrocytes should test positive for the antigen corresponding to the selected antibody in the antiserum. Thus, for example, the erythrocytes should incorporate the $Le^a$ antigen when the antiserum contains the anti-$Le^a$ antibody. The blood should receive a suitable anticoagulant, such as CPD or be defibrinated, and undergo the sensitization procedure on the day of its collection. Again, maintaining the blood at 35° to 37° C. prior to its use avoids complement fixation and a binding of cold autoantibodies.

Centrifuging the anticoagulated or defibrinated blood, at 25° to 37° C. then packs the cells. The supernatant is discarded.

The volume of packed erythrocytes undergoes resuspension in at least four volumes of saline kept warm at about 35° to 37° C. The thoroughly mixed saline suspension of erythrocytes is then centrifuged and the supernatant removed and discarded. The volume of washed and packed erythrocytes is then combined with approximately 10 volumes of the warm antiserum prepared above. Incubation then follows for 15 to 60 minutes at 37° C., during which time the suspension receives constant but gentle stirring.

By way of comparison, the procedure for sensitizing erythrocytes with the IgG protein involves placing anticoagulated whole blood into the antiserum containing the desired protein. The IgM sensitization procedure, however, removes and washes the erythrocytes prior to their addition to the reactant antiserum. This procedure gives stronger sensitization than using old blood.

After the incubation, however, the procedure for the IgM suspension exactly follows that for the IgG product. Thus, the cells undergo four washings which involves packing by centrifuation at 2° to 8° C. followed by the removal and discarding of the supernatant. The washed, sensitized erythrocytes are resuspended to a concentration of about 2 to 5 percent in a red cell preservative medium and stored at 2° to 8° C. when not in use.

Furthermore, the same procedure employed for the IgG-sensitized cells tests the IgM suspension. Each of four properly labeled test tubes receives one drop of an antihuman serum containing either anti-IgM ($\mu$-chain specific), anti-IgG ($\gamma$-chain specific), anti-C3, or anti-C4. Each of the test tubes also receives a drop of prepared sensitized-cell suspension.

The test tubes with the drop of the cell suspension and each of the appropriate antihuman serums experience centrifugation at 1000 rcf for 15 to 20 seconds. The tubes with the anti-IgG ($\gamma$-chain specific), anti-C3, and anti-C4 proteins should yield negative reactions. The test with the undiluted anti-IgM antihuman serum should yield a reaction strength of 2-4+ and at least a 1+ reaction with a 1:4 dilution of the same antiserum.

As for the IgG procedure, the reactant serum sensitizing erythrocytes with IgM may have to undergo testing in order to produce the desired reactivity. Again, that would involve preparing serial dilutions of the reactant antiserum containing the antibody of the IgM class. Each of the dilutions should proceed through the above procedure. Testing the resultant, sensitized erythrocytes would reveal the appropriate dilution for producing erythrocytes having the desired reactivity.

3. Preparation of C3-Sensitized Erythrocytes

The C3 sensitizing procedure commences with the preparation of two separate solutions containing different amounts of a phosphate buffer. Adding a portion of the second of these solutions to the first allows the achievement of a sensitizing diluent having the requisite pH for the subsequent steps.

For the first solution, 92.4 g. of reagent grade sucrose, 690 mg. $NaH_2PO_4 \cdot H_2O$ and 1578 mg. $Na_2EDTA \cdot 2H_2O$ dissolve in 800 ml. of distilled water in a one liter volumetric flask. This solution then receives sufficient additional water to bring its final volume up to the one liter mark.

To prepare the second solution, another one liter volumetric flask receives, in approximately 800 milliliters of water, 92.4 g. of reagent grade sucrose and 1578 mg. $Na_2EDTA \cdot 2H_2O$. The second solution, however, in distinction to the first, receives 710 mg. of $Na_2HPO_4$. The different phosphate salt gives the second solution a different pH than the first. After the dissolution of these ingredients into the water, the second solution receives sufficient distilled water to bring its total volume to one liter.

The second solution is slowly added to the first to adjust the pH of the latter until it reaches 5.1. A properly calibrated pH meter allows for the determination. The solution having a pH of about 5.1 then finds further use in the sensitization procedure as the required sensitizing diluent.

Nineteen volumes of the sensitizing dilient with the pH of 5.1 enters a container having a stirrer. The container should sit in an ice bath until its contents reach a temperature of 0° C.

As above, the blood providing the erythrocytes that will receive the C3 protein comes from a healthy donor, typically group O, and will have received a suitable anticoagulant, again CPD for example, or have been defibrinated. Fresh, unclotted blood may also be used. As with the prior procedures, the blood should undergo the described procedure on the day of its collection and remain at about 35° to 37° C. prior to its use.

With gentle stirring, one volume of the well mixed anticoagulated whole blood then combines with 19 volumes of the sensitizing diluent previously chilled to 0° C. The blood and the diluent then incubate together for 15 to 60 minutes at 0° C. with constant, gentle stirring.

The steps subsequent to this incubation exactly follow those given above in the prior two preparations. Thus, the cells receive four washings which consist of centrifugation at 2° to 8° C. followed by the removal and discarding of the supernatant and their subsequent resuspension in at least four volumes of red cell preservative medium at 2° to 8° C. After the last centrifugation and removal of the supernatant, the sensitized erythrocytes undergo resuspension to a concentration of 2 to 5 percent in the red cell preservative medium. This suspension should remain at 2° to 8° C. when not in use.

The sensitizing diluent does not provide C3 complement proteins which attach to the erythrocytes through this procedure. Rather, the proteins appear in the noncellular (plasma) portion of the same blood which provides the erythrocytes. The sensitizing diluent and the conditions of the incubation simply favor the attachment of the C3 complement component to the exclusion of any other proteins present. The different sensitizing diluent and incubation conditions given below in Section 4 result in the attachment to the erythrocytes of the C4 complement component in the original blood to the exclusion of other proteins contained in it.

The erythrocytes sensitized with the C3 proteins should undergo the same testing procedure given above in Sections 1 and 2 for IgG- and IgM-sensitized erythrocytes. The four test tubes will each have one drop of an antiserum containing either the anti-C3, the anti-IgG ($\gamma$-chain specific), the anti-IgM ($\mu$-chain specific), or the anti-C4 protein. They will each then receive one drop of the sensitized cell suspension and be centrifuged at 1000 rcf for 15 to 20 seconds. The test tube with the anti-C3 monospecific antihuman serum should provide a reaction strength of 2-4+. A 1:4 dilution of the same serum should provide a reaction strength of at least 1+. The other test tubes should display negative reactions.

4. Preparation of C4-Sensitized Erythrocytes

As with the procedure given above in Section 3 for the C3 sensitized erythrocytes, the present scheme also begins with the preparation of two solutions. For the first solution, 92.4 g. of reagent grade sucrose, 690 mg. of $NaH_2PO_4 \cdot H_2O$ and 526 mg. $Na_2EDTA \cdot 2H_2O$ dissolves in approximately 800 ml. of distilled water contained in one liter volumetric flask. Additional distilled water brings the total volume to exactly one liter. In comparison with the first solution for the C3 protein, the present solution contains only 526 mg. of $Na_2ED-TA \cdot 2H_2O$ while the prior solution contained three times as much, or 1578 mg.

The second solution for the C4 preparation also includes the same lesser amount of $Na_2EDTA \cdot 2H_2O$. Specifically, it has 92.4 g. reagent grade sucrose, 710 mg. $Na_2HPO_4$ and 526 mg. $Na_2EDTA \cdot 2H_2O$ with a final volume of one liter.

The sensitizing diluent results by adding the second solution to the first until a pH of 7.0 is reached. This pH compares to the value of 5.1 used for the attachment of the C3 protein.

A container with a stirrer then receives 19 volumes of the resulting sensitizing diluent having the pH of 7.0. The container remains in a water bath until its contents reach a temperature of 37° C.

Whole blood from a healthy donor, typically group O, should receive an anticoagulant, such as CPD, or have been defibrinated. Fresh, unclotted blood may also be used. It then undergoes the remaining procedures on the day of its collection. As with all of the above preparations, it should remain at a temperature of 35° to 37° C. prior to its use.

Before combining with the diluent, the blood with the anticoagulant should undergo centrifugation at 25° to 37° C. to pack the erythrocytes. The supernatant is removed and measured, with 4/5 of its original volume discarded. The remaining 1/5 volume of the supernatant then receives sufficient sterile physiologic saline solution, maintained at 35° to 37° C., to bring its volume back to the original volume of the supernatant. The packed cells then enter the diluted warm supernatant and are mixed with it to resuspend them.

With gentle stirring, one volume of the well mixed suspension of the erythrocytes in the diluted supernatant then combines with the above warm sensitizing diluent. The mixture incubates for 15 to 60 minutes at 37° C. while the gentle stirring continues. Upon the completion of the incubation, the cells undergo centrifugation at 2° to 8° C. with the subsequent removal and discarding of the supernatant.

Further comparisons with the C3 preparation follow from the listing of the above steps. The C3 sensitization procedure involves the use of fresh or defibrinated whole blood or blood merely having an anticoagulant added. To prepare the C4-sensitized erythrocytes, the blood's liquid is removed from the erythrocytes and 4/5 of its volume is replaced by the physiologic saline solution. Incubation then proceeds at 37° C. for the C4 cells rather than 0° C. for the C3-sensitized erythrocytes.

The succeeding steps, however, follow the procedures given above for all three of the prior preparations. Thus, the cells experience four washings which consist of resuspending one volume of sensitized erythrocytes and four volumes of red cell preservative medium maintained at 2° to 8° C. followed by centrifugation. Subsequent to their resuspension to a concentration of 2 to 5 percent in a red cell preservative medium, the cells remain in storage at 2° to 8° C. when not in use.

The resulting sensitized erythrocyte suspension should also undergo the same testing procedure as the other three preparations. Following the same steps as above, the anti-C4 antihuman serum, when undiluted, should give a reaction strength with the erythrocytes of 2–4+ and at least a 1+ reaction where the antiserum has undergone a 1:4 dilution. The reactions with the anti-IgG ($\gamma$-chain specific), the anti-IgM ($\mu$-chain specific), and the anti-C3 antihuman serums should produce negative reactions.

Accordingly, what is claimed is:

1. A method of preparing C3-sensitized erythrocytes comprising:
    (A) to a solution containing:
        (1) 8.0 to 10.0 w./v. percent sucrose;
        (2) a buffer in a concentration of about 0.1 to 25 millimolar; and
        (3) EDTA in a predetermined concentration within the range of about 0.10 to 50.0 millimolar,
    said solution having a pH of about 5.1 and a temperature of about 0° C., adding a predetermined amount of freshly collected erythrocyte-containing, anticoagulated, defibrinated or unclotted, fresh whole blood;
    (B) incubating said solution with said erythrocytes at about 0° C., thereby forming C3 sensitized erythrocytes;
    (C) after the step of incubating, removing said C3 sensitized erythrocytes from the solution in which they were incubated;
    (D) after the step of removing said C3 sensitized erythrocytes, washing said C3 sensitized erythrocytes; and
    (E) resuspending said washed C3 sensitized erythrocytes in a red cell preservative medium.

2. The method of claim 1 wherein said buffer is $Na_2HPO_4-NaH_2PO_4 \cdot H_2O$ and said phosphate buffer is present in said solution in a concentration of about 4.9 to 5.1 millimolar.

3. The method of claim 2 wherein said EDTA is added to said solution in the form of $Na_2EDTA \cdot 2H_2O$ in a concentration of about 2.5 to 20 millimolar.

4. The method of claim 3 wherein said concentration of $Na_2EDTA \cdot 2H_2O$ is about 8.4 millimolar.

5. The method of claim 4 wherein one volume of said blood is added to about 19 volumes of said solution.

6. The method of claim 5 wherein the step of washing said erythrocytes is performed by suspending said erythrocytes in and removing said erythrocytes from a red cell preservative medium a plurality of times.

7. The method of claim 6 wherein said blood is of an animal to which a normal human can make antibodies.

8. The method of claim 7 wherein said blood is mammalian.

9. The method of claim 8 wherein said blood is from a mammal selected from the class consisting of human, rabbit, goat, and horse.

10. The method of claim 9 wherein said blood is human blood.

11. The method of claim 10 wherein said blood is from a rabbit.

* * * * *